US008670988B2

(12) United States Patent
Yoshida

(10) Patent No.: US 8,670,988 B2
(45) Date of Patent: Mar. 11, 2014

(54) AUDIO ENCODING/DECODING APPARATUS AND METHOD PROVIDING MULTIPLE CODING SCHEME INTEROPERABILITY

(75) Inventor: Koji Yoshida, Kanagawa (JP)

(73) Assignee: Panasonic Corporation, Osaka (JP)

( * ) Notice: Subject to any disclaimer, the term of this patent is extended or adjusted under 35 U.S.C. 154(b) by 921 days.

(21) Appl. No.: 11/658,150

(22) PCT Filed: Jun. 29, 2005

(86) PCT No.: PCT/JP2005/011998

§ 371 (c)(1), (2), (4) Date: Jan. 23, 2007

(87) PCT Pub. No.: WO2006/008932

PCT Pub. Date: Jan. 26, 2006

(65) Prior Publication Data

US 2007/0299660 A1 Dec. 27, 2007

(30) Foreign Application Priority Data

Jul. 23, 2004 (JP) ................................ 2004-216127

(51) Int. Cl.
*G10L 19/00* (2013.01)
*A61K 38/16* (2006.01)

(52) U.S. Cl.
USPC ............ 704/500; 704/501; 370/466; 370/342

(58) Field of Classification Search
USPC .................................................. 704/500–503
See application file for complete search history.

(56) References Cited

U.S. PATENT DOCUMENTS 5,414,796 A * 5/1995 Jacobs et al. .................. 704/221
5,553,190 A 9/1996 Ohya et al.
5,664,057 A * 9/1997 Crossman et al. ............ 704/229
5,953,698 A 9/1999 Hayata (Continued)

FOREIGN PATENT DOCUMENTS

EP 1 094 446 4/2001
JP 2-36628 2/1990

(Continued)

OTHER PUBLICATIONS

European Office Action dated Aug. 5, 2008.

(Continued)

*Primary Examiner* — Jialong He
(74) *Attorney, Agent, or Firm* — Dickinson Wright PLLC

(57) ABSTRACT

There is provided an audio encoding device capable of causing a decoding side to freely select an audio decoding mode corresponding to a control method used for audio encoding and capable of generating data which can be decoded even when the decoding side does not correspond to the control method. The audio encoding device (100) outputs encoded data corresponding to an audio signal containing an audio component and encoded data corresponding to an audio signal containing no audio component. An audio encoding unit (102) encodes the input audio signal in a predetermined section unit and generates encoded data. An audio present/absent judgment unit (106) decides whether the input audio signal contains an audio component for each predetermined section. A bit embedding unit (104) performs synthesis of noise data only for those generated from the input audio signal of the voice absent section in the encoded data generated by the audio encoding unit (102), thereby acquiring encoded data corresponding to an audio signal containing an audio component and encoded data corresponding to an audio signal containing no audio component.

15 Claims, 11 Drawing Sheets

(56) References Cited

U.S. PATENT DOCUMENTS

| | | | | |
|---|---|---|---|---|
| 5,959,560 | A * | 9/1999 | Said et al. | 341/107 |
| 5,960,389 | A | 9/1999 | Jarvinen | |
| 6,094,636 | A * | 7/2000 | Kim | 704/500 |
| 6,606,593 | B1 | 8/2003 | Jarvinen | |
| 6,643,618 | B2 * | 11/2003 | Matsuoka et al. | 704/228 |
| 6,718,298 | B1 * | 4/2004 | Judge | 704/215 |
| 7,136,810 | B2 * | 11/2006 | Paksoy et al. | 704/219 |
| 2002/0101844 | A1 * | 8/2002 | El-Maleh et al. | 370/342 |
| 2002/0152083 | A1 * | 10/2002 | Dokic et al. | 704/500 |
| 2002/0161573 | A1 * | 10/2002 | Yoshida | 704/201 |
| 2002/0165681 | A1 * | 11/2002 | Yoshida et al. | 702/76 |
| 2002/0165720 | A1 * | 11/2002 | Johnson et al. | 704/500 |
| 2003/0093264 | A1 * | 5/2003 | Miyasaka et al. | 704/205 |
| 2004/0110539 | A1 * | 6/2004 | El-Maleh et al. | 455/563 |
| 2004/0186735 | A1 * | 9/2004 | Ferris et al. | 704/500 |
| 2005/0023343 | A1 * | 2/2005 | Tsuchinaga et al. | 235/382 |
| 2006/0098686 | A1 * | 5/2006 | Takakuwa et al. | 370/470 |
| 2006/0100859 | A1 * | 5/2006 | Jelinek et al. | 704/201 |

FOREIGN PATENT DOCUMENTS

| | | |
|---|---|---|
| JP | 5-122165 | 5/1993 |
| JP | 6-104851 | 4/1994 |
| JP | 9-97098 | 4/1997 |
| JP | 9-149104 | 6/1997 |
| JP | 10-39898 | 2/1998 |
| JP | 10-190498 | 7/1998 |
| JP | 2001-94507 | 4/2001 |
| JP | 2001-343984 | 12/2001 |
| JP | 2002-333900 | 11/2002 |
| JP | 2003-23683 | 1/2003 |
| JP | 2004-94132 | 3/2004 |
| WO | 00/34944 | 6/2000 |

OTHER PUBLICATIONS

PCT International Search Report dated Oct. 11, 2005.

3GPP TS 26.071 v5.0.0 (Jun. 2002), Technical Specification, 3rd Generation Partnership Project, Technical Specification Group Services and System Asspects, Mandatory Speech CODEC Speech Processing Functions, AMR Speech CODEC, General Description (Release 5), Global System for Mobile Communications, www.3gpp.org, Valbonne, France, pp. 1-12, Jun. 2002.

3GPP TS 26.093v6.0.0 (Mar. 2003), Technical Specification, 3rd Generation Partnership Project, Technical Specification Group Services and System Aspects, Mandatory Speech Codec Speech Processing Functions, Adaptive Multi-Rate (AMR) Speech Codec, Source Controlled Rate Operation (Release 6), Global System for Mobile Communications, www.3gpp.org, Valbonne, France, pp. 1-30, Mar. 2003.

Japanese Office Action dated Jan. 31, 2012.

* cited by examiner

FIG.5A
FIG.5B
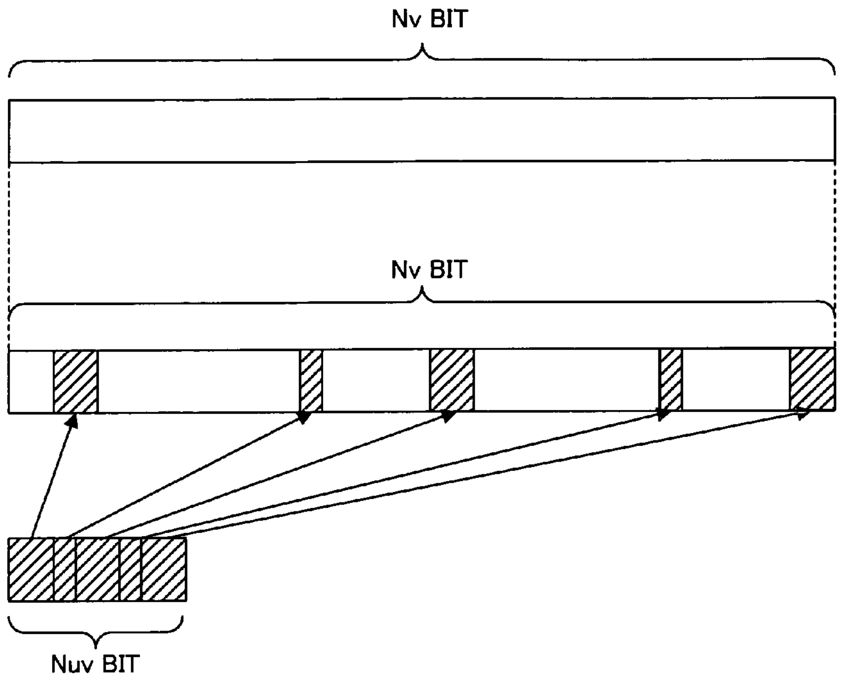
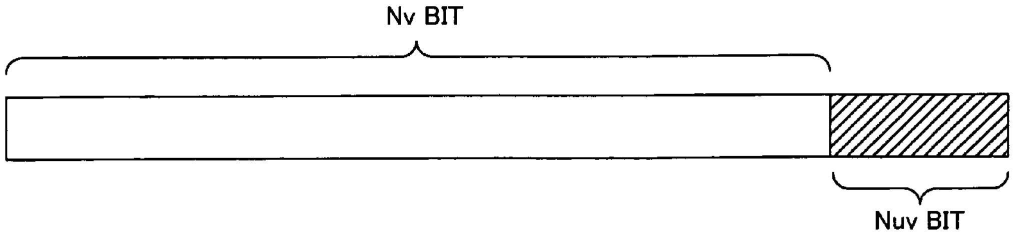
FIG.6

| CODE INDEX i (BINARY REPRESENTATION) | | | | CODE VECTOR C[i] |
|---|---|---|---|---|
| 0 | 0 | 0 | 0 | C[0] |
| 0 | 0 | 0 | 1 | C[1] |
| 0 | 0 | 1 | 0 | C[2] |
| 0 | 0 | 1 | 1 | C[3] |
| 0 | 1 | 0 | 0 | C[4] |
| 0 | 1 | 0 | 1 | C[5] |
| 0 | 1 | 1 | 0 | C[6] |
| 0 | 1 | 1 | 1 | C[7] |
| 1 | 0 | 0 | 0 | C[8] |
| 1 | 0 | 0 | 1 | C[9] |
| 1 | 0 | 1 | 0 | C[10] |
| 1 | 0 | 1 | 1 | C[11] |
| 1 | 1 | 0 | 0 | C[12] |
| 1 | 1 | 0 | 1 | C[13] |
| 1 | 1 | 1 | 0 | C[14] |
| 1 | 1 | 1 | 1 | C[15] |

RESTRICTED SEARCH RANGE

MASK BIT ASSIGNMENT

FIG.10

AUDIO ENCODING/DECODING APPARATUS AND METHOD PROVIDING MULTIPLE CODING SCHEME INTEROPERABILITY

TECHNICAL FIELD

The present invention relates to a speech coding apparatus and speech coding method, and, particularly to a speech coding apparatus and speech coding method used for transmitting coded data of different format types between an active speech section and inactive speech section.

BACKGROUND ART

In speech data communication over an IP (Internet Protocol) network, there are cases where coded data of different format types between a active speech section and inactive speech section is transmitted. "Active speech" represents that a speech signal contains speech components at a predetermined level or more. "Inactive speech" represents that a speech signal does not contain speech components at a predetermined level or more. When a speech signal contains only noise components different from speech components, this speech signal is recognized to be inactive speech. One such transmission technology includes DTX control (for example, refer to non-patent document 1 and non-patent document 2).

For example, when speech coding apparatus 10 shown in FIG. 1 carries out speech coding in a mode accompanying DTX control, at active speech/inactive speech determination section 11, whether or not a section is active speech or inactive speech is determined per section for speech signals divided per section of a predetermined length (corresponding to frame length). When active speech is determined—that is, in a case of an active speech section—coded data generated at speech coding section 12 is outputted from DTX control section 13 as an active speech frame. At this time, an active speech frame is outputted together with frame type information for reporting transmission of the active speech frame. An active speech frame has a format comprised of information for Nv bits, as shown, for example, in FIG. 2(A).

On the other hand, when inactive speech is determined—that is, in a case of an inactive speech section, inactive speech frame coding is carried out at comfortable noise coding section 14. Inactive speech frame coding is coding for obtaining a signal simulating ambient noise at an inactive speech section on a decoding side, and is coding carried out using a small amount of information—that is, a small number of bits—compared to an active speech section. Coded data generated as a result of inactive speech frame coding is outputted as a so-called SID (Silence Descriptor) frame from DTX control section 13 at a fixed period at consecutive inactive speech sections. At this time, an SID frame is outputted together with frame type information for reporting transmission of the SID frame. Further, an SID frame has a format comprised of information for Nuv bits (Nuv<Nv), as shown, for example, in FIG. 2(B).

Further, transmission of coded information is not carried out at times other than when SID frames are transmitted at an inactive speech section. In other words, transmission of inactive speech frames is omitted. However, frame type information for reporting transmission of an inactive speech frame alone is outputted from DTX control section 13. In this way, in DTX control, control is carried out so as to carry out discontinuous transmission, and an amount of information transmitted via a transmission path and an amount of information decoded on the decoding side is reduced at the inactive speech section.

Compared to this, when speech coding is carried out in a mode where DTX control is not carried out, a speech signal is always processed to be active speech, and as a result, transmission of coded data is always carried out in a consecutive manner. Therefore, with a speech coding apparatus of the related art having a DTX control function, a mode of speech coding is set in advance to a mode that is accompanied with DTX control (with DTX control) or a mode that is not accompanied with DTX control (without DTX), and speech coding is then carried out.

Non-Patent Document 1: "Mandatory speech CODEC speech processing functions; AMR speech CODEC; General description", 3rd Generation Partnership Project, TS26.071

Non-Patent Document 2: "Mandatory speech codec speech processing functions Adaptive Multi-Rate (AMR) speech codec; Source controlled rate operation", 3rd Generation Partnership Project, TS26.093

DISCLOSURE OF INVENTION

Problems to be Solved by the Invention

However, with a speech coding apparatus of the related art described above, an outputted coded data series has a difference between a case with DTX control and a case without DTX control. For example, in a mode without DTX control, there is one type of format for coded data constituting the coded data. Compared to this, in a mode with DTX control, there are two types of format for coded data that is actually transmitted, with three types of format existing in practical terms. In accordance with this kind of difference, when DTX control is carried out on the coding side, the decoding side needs to carry out speech decoding in a mode corresponding to speech coding with DTX control. Further, when DTX control is not carried out on the coding side, speech decoding needs to be carried out in a mode corresponding to speech coding without DTX control. In other words, a speech decoding mode set at the decoding side is restricted to a speech coding mode set at the coding side, the decoding side cannot select a speech decoding mode.

Namely, with respect to a speech decoding apparatus compatible with DTX control, when coded data generated in a mode without DTX control is transmitted, even if an original speech signal of certain coded data is inactive speech, it is not possible to reduce the amount of information decoded in an inactive speech section—that is, it is not possible to improve transmission efficiency on a network—and this speech decoding apparatus is therefore not able to reduce the processing load. On the other hand, when coded data generated in a mode with DTX control is transmitted, the degree of freedom of service selection (for example, a high sound quality reception mode obtained by decoding all sections as active speech) at a speech decoding apparatus is restricted.

Further, with regards to a speech decoding apparatus that is not compatible with DTX control, when coded data obtained by a mode with DTX control is transmitted, this speech decoding apparatus cannot decode the received coded data.

Therefore, for example, when a speech coding apparatus carries out multicasting for a plurality of speech decoding apparatuses including apparatuses compatible with DTX control and apparatuses incompatible with DTX control, any of the above problems may occur even if speech coding is carried out in a mode with DTX control or speech coding is carried out in a mode without DTX control.

It is therefore an object of the present invention to provide a speech coding apparatus and a speech coding scheme that are able to allow a decoding side to select a speech decoding mode corresponding to a control scheme used in accordance with speech coding, and generate decodable data even when the decoding side is not corresponding to that control scheme.

Means for Solving the Problem

A speech coding apparatus of the present invention is a speech coding apparatus for outputting first coded data corresponding to a speech signal that contains a speech component and second coded data corresponding to a speech signal that does not contain the speech component, and has a configuration having: a coding section that encodes an inputted speech signal in predetermined section units and generates coded data; a determination section that determines whether or not the inputted speech signal contains the speech component per predetermined section; and a synthesis section that obtains the first coded data and the second coded data by carrying out synthesis of noise data for, of the coded data, only coded data generated from the inputted speech signal of an inactive speech section determined not to contain the speech component.

A speech decoding apparatus having: a first decoding section that decodes coded data in which noise data is synthesized and generates a first decoded speech signal; a second decoding section that decodes only the noise data and generates a second decoded signal; and a selection section that selects one of the first decoded speech signal and the second decoded speech signal.

A speech coding method of the present invention is a speech coding apparatus for outputting first coded data corresponding to a speech signal that contains a speech component and second coded data corresponding to a speech signal that does not contain the speech component, and has: a coding step of coding an inputted speech signal in predetermined section units and generates coded data; a determination step of determining whether or not the inputted speech signal contains the speech component per predetermined section; and a synthesizing step of obtaining the first coded data and the second coded data by carrying out synthesis of noise data for, of the coded data, only coded data generated from the inputted speech signal of an inactive speech section determined not to contain the speech component.

A speech decoding method having: a first decoding step of decoding coded data in which noise data is synthesized and generates a first decoded speech signal; a second decoding step of decoding only the noise data and generates a second decoded signal; and a selection step of selecting one of the first decoded speech signal and the second decoded speech signal.

Advantageous Effect of the Invention

According to the present invention, it is possible to allow a decoding side to select a speech decoding mode corresponding to a control scheme used in accordance with speech coding, and generate decodable data even when the decoding side is not corresponding to that control scheme.

BRIEF DESCRIPTION OF THE DRAWINGS

FIG. 5 is a diagram showing an example of a format type of Embodiment 1 of the present invention;

FIG. 6 is a diagram showing a modified example of a format type of Embodiment 1 of the present invention;

FIG. 10 is a diagram illustrating the operations of a first coding candidate generation section of Embodiment 2 of the present invention;

BEST MODE FOR CARRYING OUT THE INVENTION

Embodiments of the present invention will be described below in detail using the accompanying drawings.

Embodiment 1

Figure 1:
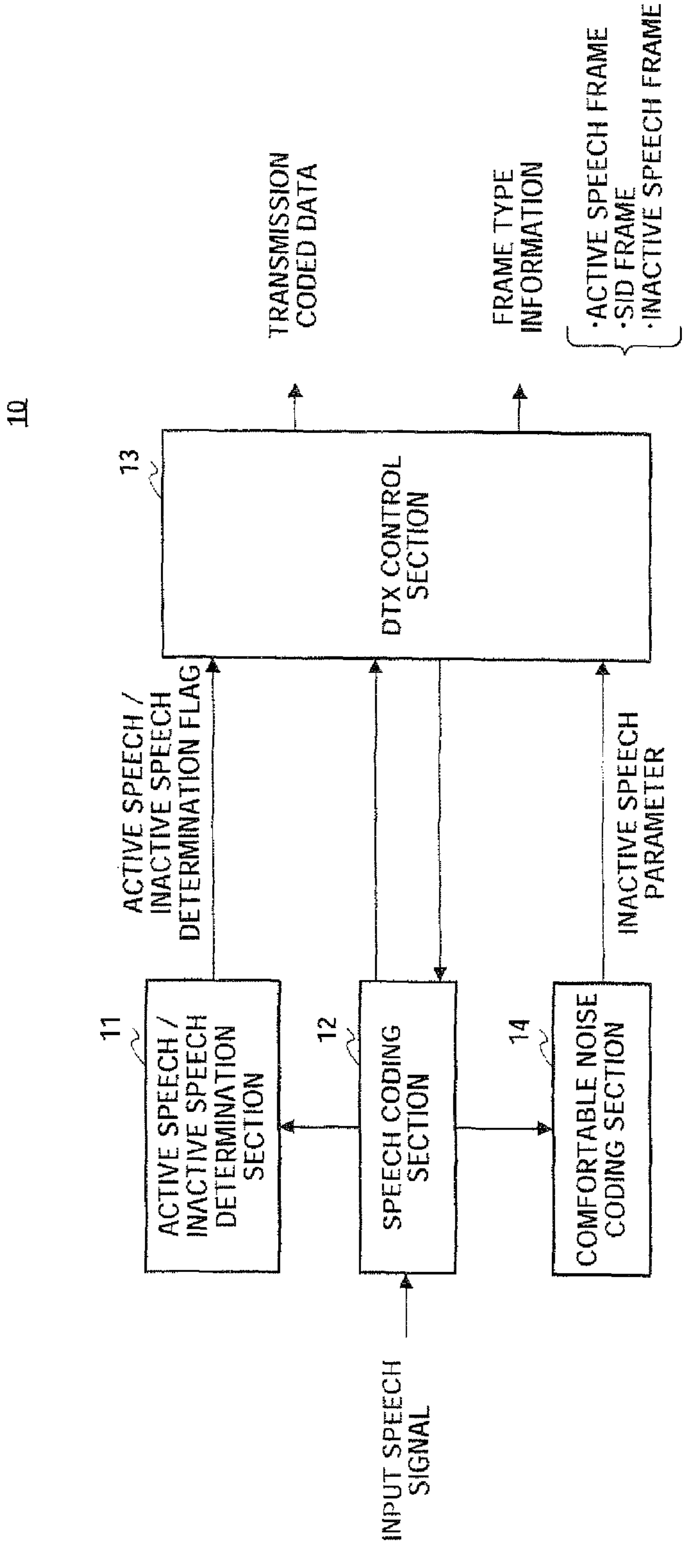
FIG.1 PRIOR ART
FIG. 1 is a block diagram showing an example of a configuration of a speech coding apparatus of the related art.
Figures 2A, 2B:
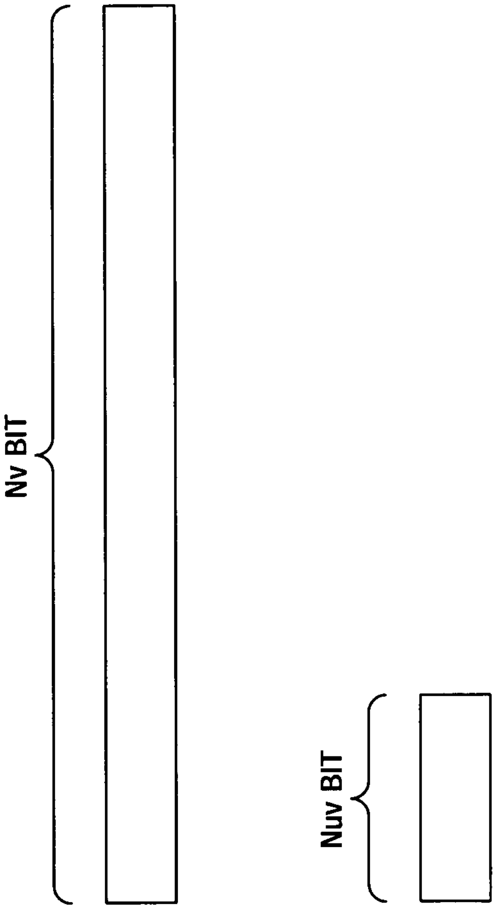
FIG.2B PRIOR ART
FIG. 2 is a diagram showing an example of a configuration of an active speech frame of the related art and an example of a configuration of a so-called SID frame of the related art.
Figure 3:
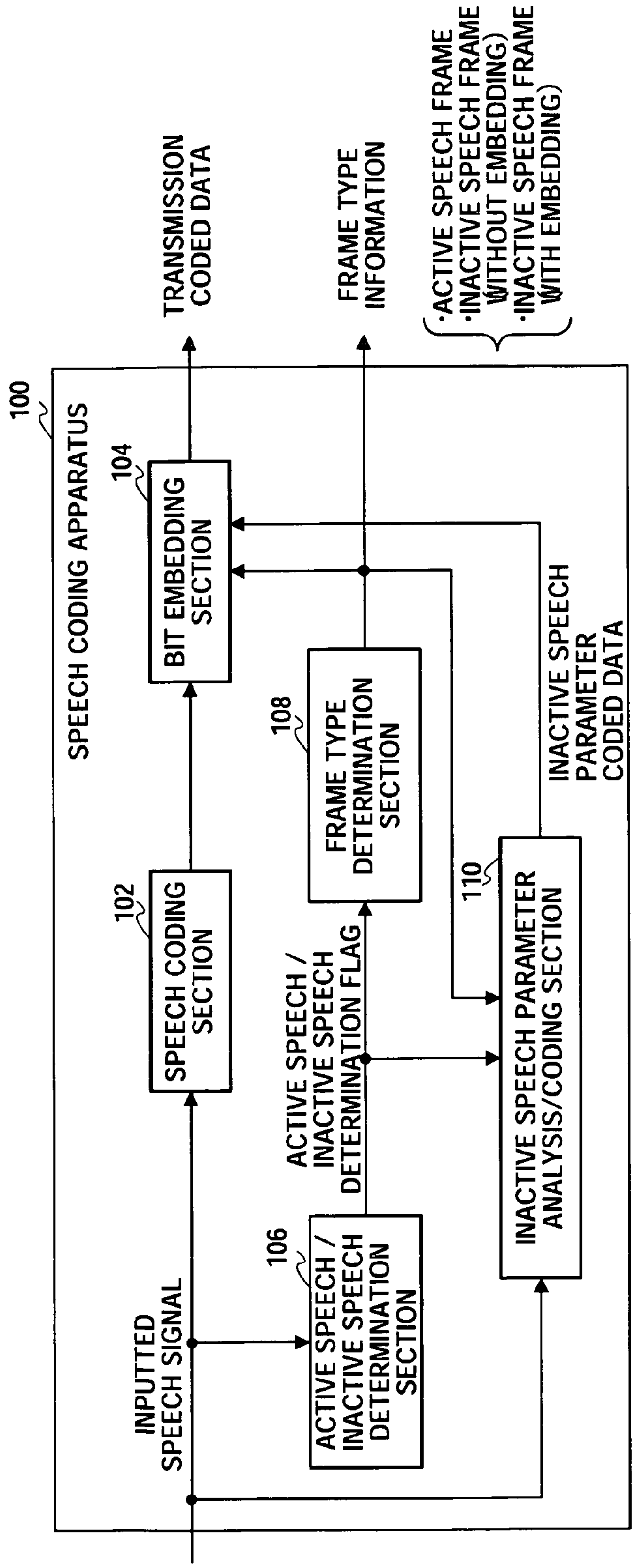
FIG. 3 is a block diagram showing a configuration of a speech coding apparatus of Embodiment 1 of the present invention.
Figure 4A:
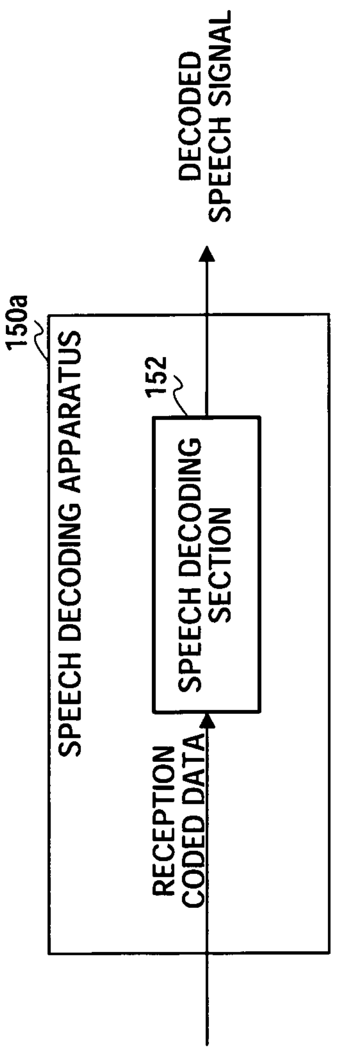
FIG. 4A is a block diagram showing an example configuration of a speech decoding apparatus of Embodiment 1 of the present invention.
Figure 4B:
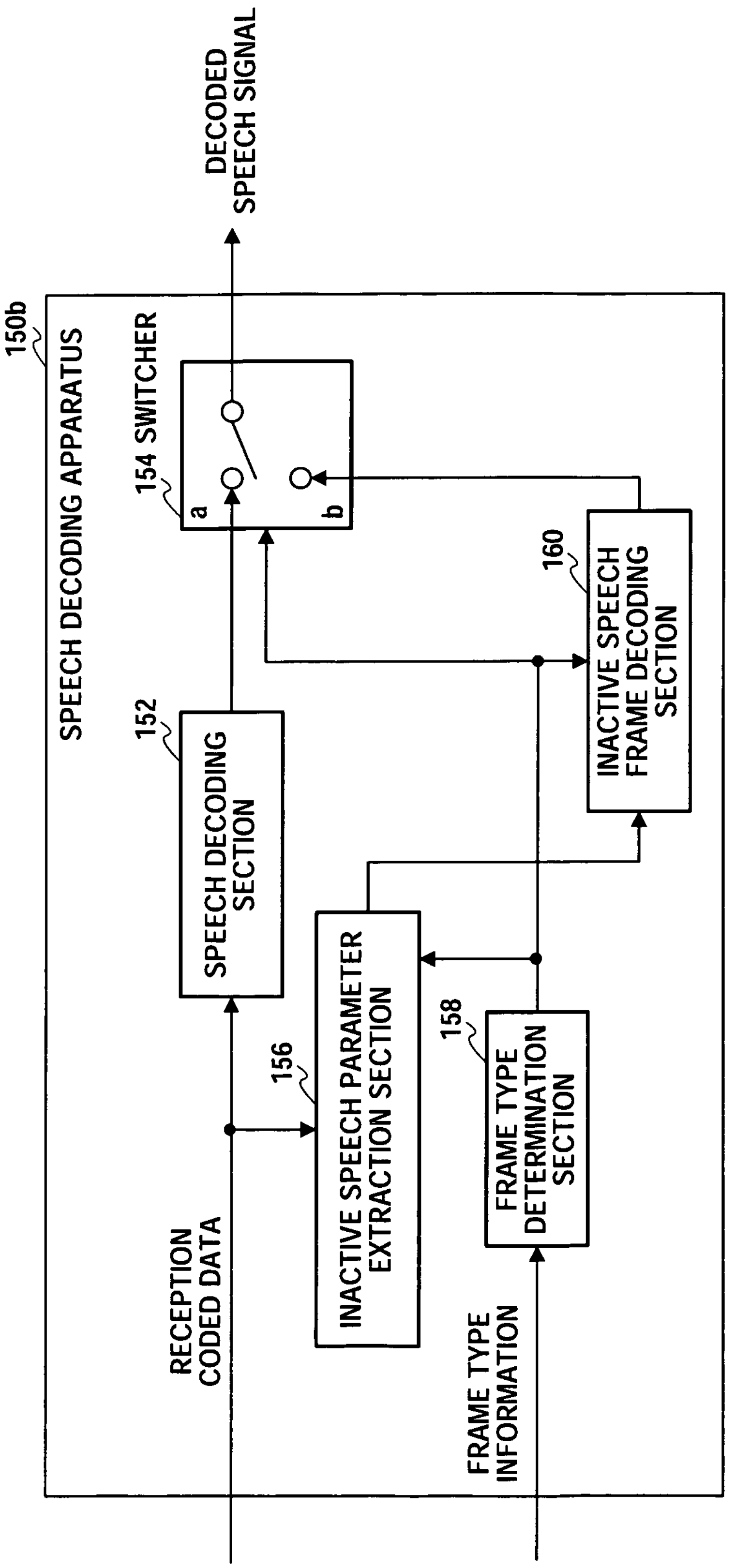
FIG. 4B is a block diagram showing another example configuration of a speech decoding apparatus of Embodiment 1 of the present invention.

FIG. 3 is a block diagram showing a configuration of a speech coding apparatus of Embodiment 1 of the present invention. Further, FIG. 4A is a block diagram showing an example of a configuration of a speech decoding apparatus of this embodiment, and FIG. 4B is a block diagram showing another example of a configuration of a speech decoding apparatus of this embodiment.

First, the configuration of speech coding apparatus 100 shown in FIG. 3 will be described. Speech coding apparatus 100 has speech coding section 102; bit embedding section 104; active speech/inactive speech determination section 106; frame type determination section 108; and inactive speech parameter analysis/coding section 110.

Speech coding section 102 encodes an inputted speech signal in units of section (frame) of a predetermined length, and generates coded data comprised of a coded bit stream of a plurality of (for example, Nv) bits. Speech coding section 102 generates coded data by arranging a coded bit stream of Nv bits obtained at the time of coding so that the format of the generated coded data is always the same. Further, the number of bits of coded data is determined in advance.

Active speech/inactive speech determination section 106 determines whether or not an inputted speech signal contains speech components per section described above, and outputs an active speech/inactive speech determination flag indicating this determination result to frame type determination section 108 and inactive speech parameter analysis/coding section 110.

Frame type determination section 108 decides coded data generated by speech coding section 102 to be one of three frame types, that is, (a) active speech frame; (b) inactive speech frame (with embedding); and (c) inactive speech frame (without embedding), using an inputted active speech/inactive speech determination flag.

More specifically, when a active speech/inactive speech determination flag indicates active speech, (a) active speech frame is decided. Further, when a active speech/inactive speech determination flag indicates inactive speech, (b) inactive speech frame (with embedding) or (c) inactive speech frame (without embedding) is decided.

Further, when active speech/inactive speech determination flags indicating inactive speech are consecutive—in other words, when inactive speech sections continue—frames (coded data) per fixed period alone are decided to be (b) inactive speech frames (with embedding), and other than these are decided to be (c) inactive speech frames (without embedding). Alternatively, when active speech/inactive speech determination flags indicating inactive speech are consecutive, (b) inactive speech frame (with embedding) is decided only when signal characteristics of an inputted speech signal changes, and other than this being decided to be (c) soundless frame (without embedding). In this way, it is possible to reduce the embedding processing load at bit embedding section 104. The determined result is then outputted as frame type information. Frame type information is information reported to inactive speech parameter analysis/coding section 110 and bit embedding section 104, and is information transmitted together with coded data.

Inactive speech parameter analysis/coding section 110 generates inactive speech parameter coded data as simulated noise data when the inputted speech signal is determined to be inactive speech by active speech/inactive speech determination section 106—that is, in a case of an inactive speech section.

More specifically, assume that information obtained by averaging the signal characteristics of the inputted speech signal in consecutive inactive speech sections is an inactive speech parameter. As information included an inactive speech parameter, for example, spectral shape information, energy of the speech signal, and gain information of an excitation signal in LPC (Linear Predictive Coding) spectral synthesis may be included.

Inactive speech parameter analysis/coding section 110 encodes an inactive speech parameter using a smaller number of bits (for example, Nuv bits) than that of the inputted speech signal of an active speech section and generates inactive speech parameter coded data. Namely, the number of bits of inactive speech parameter coded data is smaller than the number of bits of an inputted speech signal coded by speech coding section 102 (Nuv<Nv). The generated inactive speech parameter coded data is outputted when frame type information outputted from frame type determination section 108 indicates an inactive speech frame (with embedding).

Bit embedding section 104 outputs coded frames outputted from speech coding section 102 when frame type information outputted from frame type determination section 108 indicates an active speech frame or an inactive speech frame (without embedding). Accordingly, as shown in FIG. 5(A), the format of coded data outputted in this case is the same as the format of coded data generated by speech coding section 102.

On the other hand, when frame type information outputted from frame type determination section 108 indicates an inactive speech frame (with embedding), inactive speech parameter coded data outputted from inactive speech parameter analysis/coding section 110 is embedded in coded data outputted from speech coding section 102. Coded data embedded with inactive speech parameter coded data is then outputted. As shown in FIG. 5(B), coded data outputted in this case has a format type where inactive speech parameter coded data is embedded at a predetermined position within coded data generated by speech coding section 102.

In this way, inactive speech parameter coded data is embedded in coded data, so that it is possible to transmit coded data without changing the frame size of the coded data. Further, inactive speech parameter coded data is embedded in a predetermined position of the coded data, so that it is possible to simplify control processing at the time of embedding inactive speech parameter coded data.

More specifically, bit embedding section 104 replaces Nuv bits arranged in a predetermined position among the Nv bits of coded data, with inactive speech parameter coded data comprised of Nuv bits. By this means, it is possible to transmit inactive speech parameter coded data in place of some of the bits of coded data obtained by coding. Further, part of the coded data comprised of Nv bits is replaced with inactive speech parameter coded data, so that it is possible to transmit both remaining bits of coded data and inactive speech parameter coded data.

Alternatively, bit embedding section 104 overwrites Nuv bit arranged in a predetermined position among the Nv bits of coded data, with inactive speech parameter coded data comprised of Nuv bits. By this means, it is possible to delete some of the bits of coded data obtained by coding and transmit inactive speech parameter coded data. Further, part of the coded data comprised of Nv bits is overwritten with inactive speech parameter coded data, so that it is possible to transmit both remaining bits of coded data and inactive speech parameter coded data.

Replacing or overwriting of bits is effective particularly l when the influence on quality of the decoded speech signal is low even if this is carried out, or when bits of a low degree of importance are included in a coded bit stream obtained at the time of coding.

Further, with this embodiment, a case has been described where inactive speech parameter coded data is embedded by replacing or overwriting the bits obtained at the time of coding. However, as shown in FIG. 6, Nuv bits of inactive speech parameter coded data may be added to the end of a bit stream of Nv bits obtained at the time of coding, instead of embedding the inactive speech parameter coded data. Namely, bit embedding section 104 synthesizes inactive speech parameter coded data and coded data by embedding and adding inactive speech parameter coded data. As a result, frame format switching control is carried out so as to acquire coded data having different types of format between cases where this synthesis is carried out and where this synthesis is not carried out. By this means, although the frame types are different between when inactive speech parameter coded data is synthesized in coded data and when the inactive speech parameter coded data is not synthesized in the coded data, it is possible to transmit a coded data series without changing the basic frame configuration.

Further, when inactive speech parameter coded data is added, the frame size of the coded data changes, so that it is therefore preferable to transmit information relating to the frame size together with the coded data in an arbitrary format.

Further, in this embodiment, a case has been described where inactive speech parameter coded data is embedded in a predetermined position of coded data. However, the method of embedding the inactive speech parameter coded data is by no means limited to that described above. For example, bit embedding section 104 may also adaptively decide the position where inactive speech parameter coded data is embedded each time embedding is carried out. In this case, it is possible to adaptively change the position of bits subjected to replacement or the position of bits subjected to overwriting according to, for example, sensitivity and importance of the bits.

Next, the configurations of speech decoding apparatus 150*a* and 150*b* shown in FIG. 4A and FIG. 4B will be described. Although speech decoding apparatus 150*a* has a configuration having no function compatible with frame format switching control of speech coding apparatus 100, speech decoding apparatus 150*b* has a configuration having this function.

Speech decoding apparatus 150*a* shown in FIG. 4A has speech decoding section 152.

Speech decoding section 152 receives coded data transmitted from speech coding apparatus 100 via a transmission path. Further, decoding is carried out on received coded data in frame units. More specifically, a decoded speech signal is generated by decoding coded data constituting reception coded data. Received coded data contains coded data, format of which changes depending on whether or not inactive speech parameter coded data is synthesized in. However, coded data where the basic frame configuration does not change is consecutively transmitted, so that speech decoding apparatus 150*a* incompatible with frame format switching control can decode coded data received from speech coding apparatus 100.

Speech decoding apparatus 150*b* shown in FIG. 4B has: speech decoding section 152 that is the same as one provided in speech decoding apparatus 150*a*; and, in addition, switcher 154; inactive speech parameter extraction section 156; frame type determination section 158; and inactive speech frame decoding section 160.

Inactive speech parameter extraction section 156 extracts inactive speech parameter coded data synthesized in coded data transmitted as inactive speech frames (with embedding) out of coded data constituting received coded data.

Frame type determination section 158 receives frame type information transmitted from speech coding apparatus 100, and determines which of the three types of frame type the received coded data corresponds to. The determination result is reported to switcher 154 and inactive speech frame decoding section 160.

When information indicated in the frame type information is an inactive speech frame, inactive speech frame decoding section 160 decodes only inactive speech parameter coded data extracted by inactive speech parameter extraction section 156. By this means, information contained in the inactive speech parameters (for example, spectral shape information and energy) is acquired. Decoded speech signals at all of the inactive speech frames including the inactive speech frames (with embedding) and inactive speech frames (without embedding) are then generated using the acquired information.

Switcher 154 switches over an output of speech decoding apparatus 150*b* in accordance with determination results reported by frame type determination section 158. For example, when information indicated in the frame type information is an active speech frame, connection is controlled so that a decoded speech signal generated by speech decoding section 152 is an output of speech decoding apparatus 150*b*. Namely, as shown in FIG. 4B, a connection with an output of speech decoding apparatus 150*b* is switched over to a side a. On the other hand, when the indicated information is an inactive speech frame, connection is controlled so that a decoded speech signal generated by inactive speech frame decoding section 160 is an output of speech decoding apparatus 150*b*. Namely, a connection with an output of speech decoding apparatus 150*b* is switched over to a side b.

The connection switching control described above is carried out in order to switch decoding target depending on the frame type of the transmitted coded data. However, switcher 154 is able to always fix connection with an output of speech decoding apparatus 150*b* to the side a without carrying out control depending on the frame type of the transmitted coded data. Speech decoding apparatus 150*b* selects whether to carry out connection switching control depending on the frame type or whether to carry out always fixed connection. By this means, speech decoding apparatus 150*b* is able to select one of decoding coded data in a state where inactive speech parameter coded data is synthesized, and selectively decoding synthesized inactive speech parameters.

Next, the inactive speech parameter coded data embedding operations at speech coding apparatus 100 having the above configuration will be described.

At speech coding section 102, speech coding of an input speech signal is carried out and coded data is generated. Further, frame type determination of the inputted speech signal is carried out.

When the coded data is decided to be an active speech frame, as a result of the frame type determination, inactive speech parameter coded data embedding is not carried out at bit embedding section 104, and, as a result, coded data of the format shown in FIG. 5(A) is obtained. Further, when the coded data is decided to be an inactive speech frame (without embedding), inactive speech parameter coded data embedding is not carried out, and, as a result, coded data of the format shown in FIG. 5(A) is obtained. On the other hand, when the coded data is decided to be an inactive speech frame (with embedding), inactive speech parameter coded data embedding is carried out, and, as a result, coded data of the format shown in FIG. 5(B) is obtained.

In this way, according to this embodiment, by synthesizing inactive speech parameter coded data in only coded data as an inactive speech frame (with embedding) of the coded data, coded data corresponding to a speech signal containing a speech component and coded data corresponding to a speech signal that does not contain speech components are obtained—that is, inactive speech parameter coded data is synthesized in the coded data, so that it is possible to consecutively transmit coded data of different format types and yet having the same frame configurations to the decoding side. Accordingly, when coded data generated in a mode such that inactive speech parameter coded data is synthesized in coded data is transmitted to a decoding side, the decoding side can decode the coded data in which inactive speech parameter coded data remains synthesized. Namely, on the coding side, it is possible to generate data decodable even when the decoding side is incompatible with the control scheme used in accordance with the speech coding. Further, in the above case, the decoding side can select decoding coded data in a state where inactive speech parameter coded data remains synthesized or selectively decoding synthesized inactive speech parameter coded data. Namely, on the coding side, it is possible to make the speech decoder select a speech decoding mode corresponding to a control scheme used in accordance with speech coding.

Embodiment 2

Figure 7:
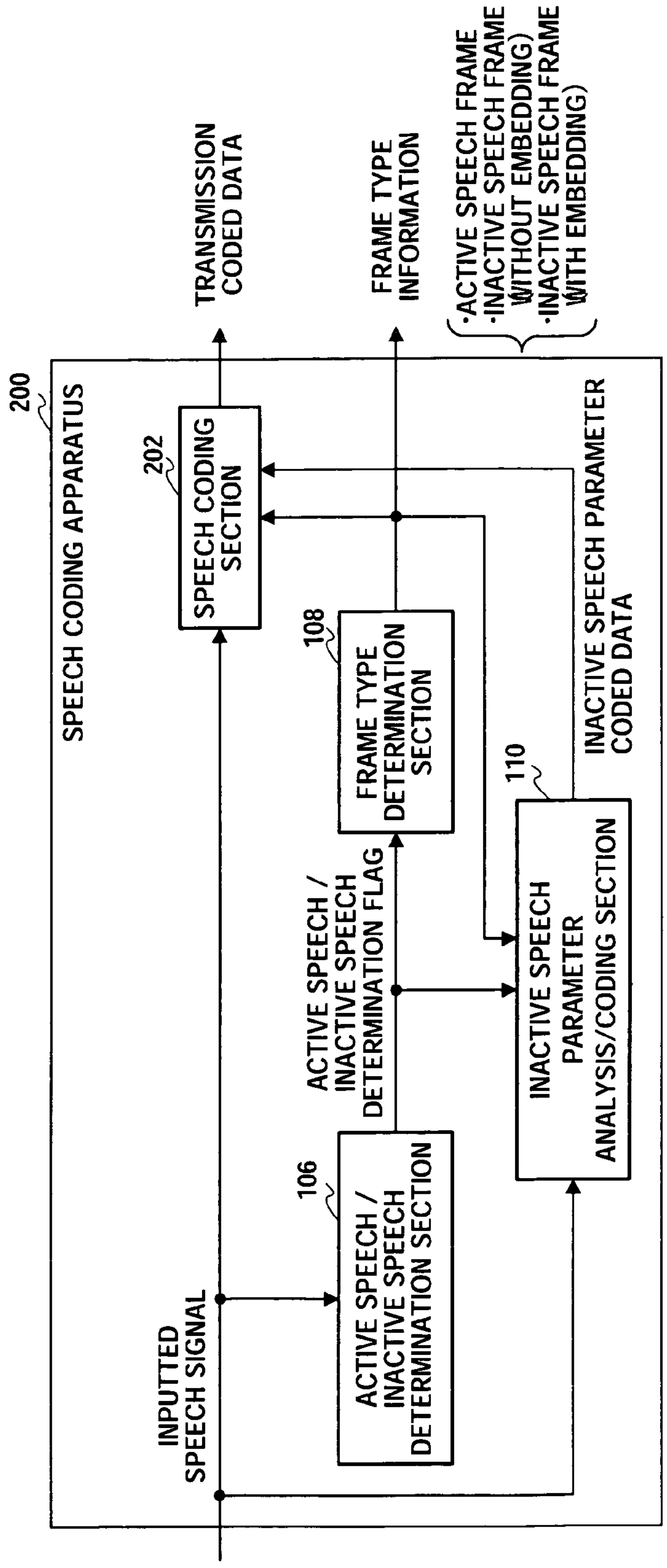
FIG. 7 is a block diagram showing a configuration of a speech coding apparatus of Embodiment 2 of the present invention.

FIG. 7 is a block diagram showing a configuration of a speech coding apparatus of Embodiment 2 of the present invention. A speech coding apparatus 200 described in this embodiment has the same basic configuration as speech coding apparatus 100 described in Embodiment 1, the components are assigned the same reference codes, and their detailed descriptions will be omitted. Further, coded data sent from speech coding apparatus 200 can be decoded at speech decoding apparatus 150*a* and 150*b* described in Embodiment 1, and the description of the speech decoding apparatus will therefore be omitted.

Speech coding apparatus 200 has a configuration having speech coding section 202 in place of speech coding section 102 and bit embedding section 104 provided in speech coding apparatus 100.

Speech coding section 202 executes the operations that combines the operations of speech coding section 102 and the operations of bit embedding section 104. Further, CELP (Code Excited Linear Prediction) coding that is able to efficiently encode an inputted speech signal is applied at speech coding section 202.

Figure 8:
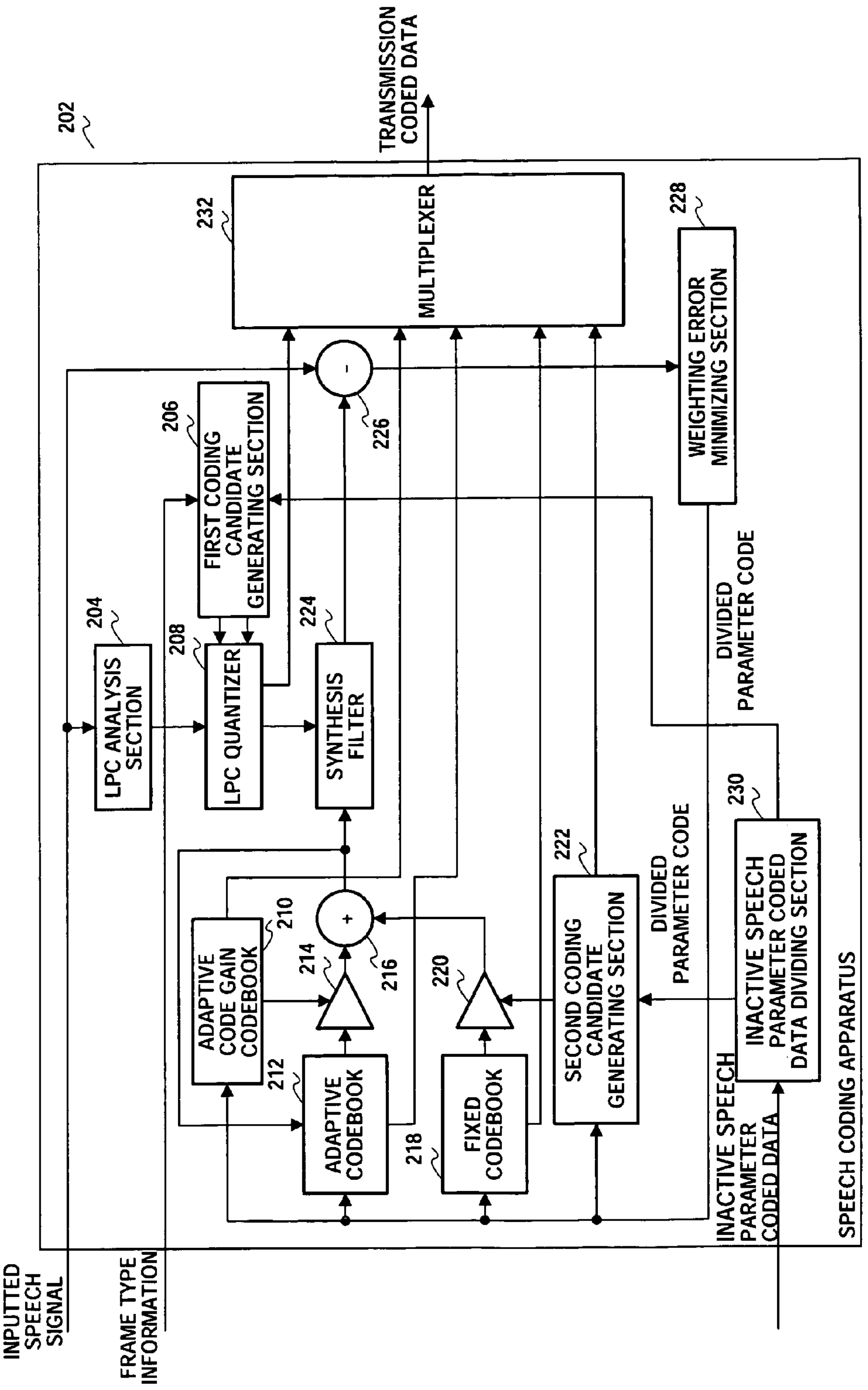
FIG. 8 is a block diagram showing a configuration of a speech coding section of Embodiment 2 of the present invention.

As shown in FIG. 8, speech coding section 202 has: LPC analysis section 204; first coding candidate generating section 206; LPC quantizer 208; adaptive code gain codebook 210; adaptive codebook 212; multiplier 214; adder 216; fixed codebook 218; multiplier 220; second coding candidate generating section 222; synthesis filter 224; subtractor 226; weighting error minimizing section 228; inactive speech parameter coding data dividing section 230; and multiplexor 232.

LPC analysis section 204 carries out linear predictive analysis using an inputted speech signal and outputs the results of this analysis, that is, an LPC coefficient, to LPC quantizer 208.

LPC quantizer 208 performs vector quantization on LPC coefficients outputted from LPC analysis section 204 based on coded candidate values and coded candidate code outputted from first coding candidate generating section 206. LPC quantization code obtained as a result of vector quantization is then outputted to multiplexer 232. Further, LPC quantizer 208 obtains decoding LPC coefficients from the LPC coefficients and outputs this decoded LPC coefficients to synthesis filter 224.

Figure 9:
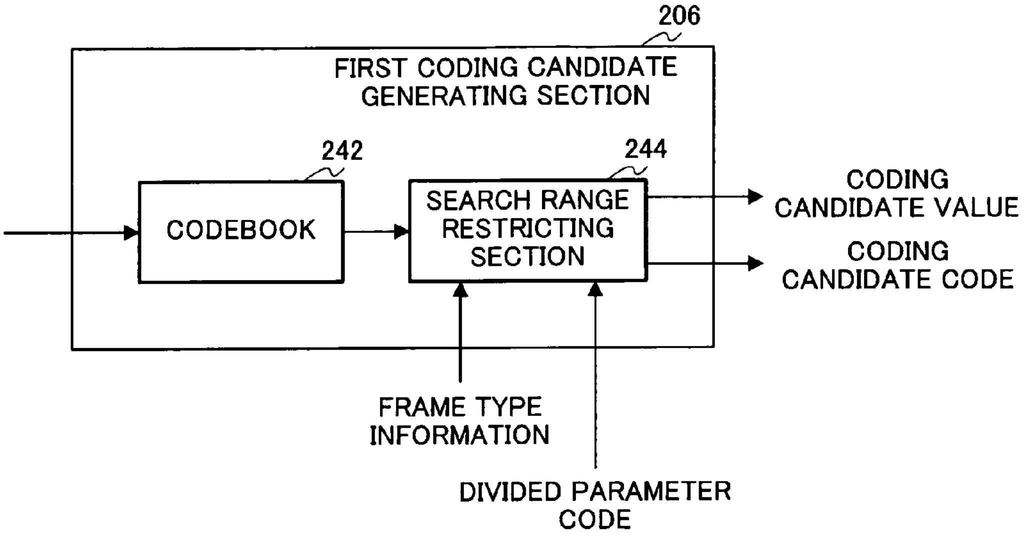
FIG. 9 is a block diagram showing a configuration of a first coding candidate generation section of Embodiment 2 of the present invention.

As shown in FIG. 9, first coding candidate generating section 206 has a codebook 242 and a search range restricting section 244, generates coding candidate values and coding candidate code used in vector quantization of LPC coefficients carried out at LPC quantizer 208 when speech coding is performed on an inputted speech signal, and outputs these to LPC quantizer 208.

Codebook 242 holds a list of coding candidate values and coding candidate code in advance that can be used at LPC quantizing section 208 at the time of coding a speech signal. Search range restricting section 244 generates coding candidate values and coding candidate code used at LPC quantizer 208 at the time of coding an input speech signal. More specifically, when frame type information from frame type determination section 108 indicates "active speech frame" or "inactive speech frame (without embedding)," search range restricting section 244 does not carry out restriction of search range on coding candidate values and coding candidate code held in advance in codebook 242. On the other hand, when the frame type information indicates "inactive speech frame (with embedding)," search range restricting section 244 carries out restriction of the search range on the coding candidate values and coding candidate code. The restricted search range is decided by assigning mask bits based on the number of bits of divided parameter code obtained from inactive speech parameter coding data dividing section 230 and by embedding divided parameter code in accordance with the assignment of mask bits.

Synthesis filter 224 carries out filter synthesis using decoded LPC coefficients outputted from LPC quantizer 208 and an excitation outputted from adder 216, and outputs a synthesized signal to subtractor 226. Subtractor 226 calculates an error signal between the synthesized signal outputted from synthesis filter 224 and the inputted speech signal, and outputs this to weighting error minimizing section 228.

Weighting error minimizing section 228 assigns a perceptual weighting to an error signal outputted from subtractor 226, and calculates distortion of the inputted speech signal and the synthesized signal at an auditory weighted region. Signals to be generated by adaptive codebook 212, fixed codebook 218, and second coding candidate generating section 222 are then decided so as to minimize this distortion.

More specifically, weighting error minimizing section 228 selects adaptive excitation lag that minimizes distortion from adaptive codebook 212. Further, a fixed excitation vector that minimizes distortion is selected from fixed codebook 218. Moreover, quantized adaptive excitation gain that minimizes distortion is selected from adaptive code gain codebook 210. Further, quantized fixed excitation gain is selected from second coding candidate generating section 222.

Adaptive codebook 212 has a buffer, stores an excitation outputted by adder 216 in that buffer, cuts out one frame worth of a sample from the buffer from a cut-out position specified by a signal outputted from weighting error minimizing section 228, and outputs this to multiplier 214 as an adaptive excitation vector. Further, adaptive excitation lag code indicating the decision result is outputted to multiplexor 232. Moreover, adaptive codebook 212 updates the excitation stored in the buffer per receiving an excitation outputted from adder 216.

Adaptive code gain codebook 210 decides quantized adaptive excitation gain based on a signal outputted from weighting error minimizing section 228 and outputs this to multiplier 214. Further, quantized adaptive excitation gain code indicating this decision result is outputted to multiplexor 232.

Multiplier 214 multiplies quantized adaptive excitation gain outputted from adaptive code gain codebook 210 with an adaptive excitation vector outputted from adaptive codebook 212, and outputs the multiplication result to adder 216.

Fixed codebook 218 decides a vector having a shape specified by a signal outputted from weighting error minimizing section 228 to be a fixed excitation vector, and outputs this to multiplier 220. Further, this fixed excitation vector code indicating the decision result is outputted to multiplexor 232.

Multiplier 220 multiplies the quantized fixed excitation gain outputted from second coding candidate generating section 222 with a fixed excitation vector outputted from fixed codebook 218, and outputs the multiplication result to adder 216.

Adder 216 adds an adaptive excitation vector outputted from multiplier 214 and a fixed excitation vector outputted from multiplier 220, and outputs an excitation that is the addition result to synthesis filter 224 and adaptive codebook 212.

Inactive speech parameter coding data dividing section 230 divides inactive speech parameter coded data outputted from inactive speech parameter analysis/coding section 110. Inactive speech parameter coded data is then divided per number of bits of quantization code in which the inactive speech parameter coded data is embedded. Further, LCP quantization code in frame units and quantized fixed excitation gain code in subframe units is assigned to quantization code of the embedding target. As a result, inactive speech parameter coding data separation section 230 divides inactive speech parameter coded data into (1+the number of subframes), and obtains the divided parameter codes of this number.

Second coding candidate generating section 222 has a fixed code gain codebook, and generates candidates for quantized fixed excitation gain multiplied with fixed excitation vectors at the time of carrying out speech coding. More specifically, when frame type information from frame type determination section 108 indicates "active speech frame" or "inactive speech frame (without embedding)," second code candidate generating section 222 does not carry out search range restriction for quantized fixed excitation gain candidates stored in a fixed code gain codebook in advance. On the other hand, when the frame type information indicates "inactive speech frame (with embedding)," second coding candidate generating section 222 carries out search range restriction on quantized fixed excitation gain candidates. The restricted search range is decided by assigning mask bits based on the number of bits of divided parameter code obtained from inactive speech parameter coding data dividing section 230 and by embedding divided parameter code in accordance with the assignment of mask bits. In this way, quantized fixed excitation gain candidates are generated. Then, a candidate specified based on a signal from weighting error minimizing section 228 from generated quantized fixed excitation gain candidates is decided as quantized fixed excitation gain to be multiplied with a fixed excitation vector, and is outputted to multiplier 220. Further, quantized fixed excitation gain code indicating this decision result is outputted to multiplexor 232.

Multiplexor 232 multiplexes an LPC quantization code from LPC quantization section 208, a quantized adaptive excitation gain code from adaptive code gain codebook 210, an adaptive excitation vector code from adaptive codebook 212, a fixed excitation vector code from fixed codebook 218, and a quantized fixed excitation gain code from second coding candidate generating section 222. Coded data is then obtained by this multiplexing.

Next, the search range restricting operations at speech coding section 202 will be described. Here, an example of the search restricting operations at first coding candidate generating section 206 will be described.

At speech coding section 202, as shown in FIG. 10, codebook 242 stores combinations of sixteen code indexes i and code vectors C[i] corresponding to each code index i as coded candidate codes and coded candidate values.

When frame type information from frame type determination section 108 indicates "active speech frame" or "inactive speech frame (without embedding)", search range restricting section 244 outputs combinations of the sixteen candidates to LPC quantizer 208 without restricting the search range.

On the other hand, when the frame type information indicates "inactive speech frame (embedding)," search range restricting section 244 assigns mask bits to code index i based on the number of bits of divided parameter code obtained from inactive speech parameter coding data dividing section 230. In this embodiment, a predetermined number of coded bits having bit sensitivity lower than a predetermined level or a predetermined number of bits including a coded bit having the lowest bit sensitivity is subjected to be switching and masking. For example, when a quantized value of a scalar value corresponds with a code in ascending order, mask bits are assigned from the LSB (Least Significant Bit). The search range is restricted by carrying out this kind of mask bit assignment. Namely, codebook is restricted in advance, premised on embedding. Accordingly, it is possible to prevent deterioration of coding performance due to embedding.

Search candidates belonging to a restricted search range are then specified by embedding a divided parameter code in bits masked at mask bit assignment. In the example shown here, mask bits are assigned to the lower two bits, so that the search range is restricted from the original sixteen candidates to four candidates. Combinations of these four candidates are then outputted to LPC quantizer 208.

According to this embodiment, optimum quantization is carried out assuming the embedding of inactive speech parameter coded data. Namely, among the plurality of bits constituting coded data as an inactive speech frame, a predetermined number of bits having sensitivity of a predetermined level or less, or a predetermined number of bits including a bit having the lowest sensitivity is subjected to mask bit assignment and divided parameter code embedding. Accordingly, it is possible to reduce the influence on the quality of the decoded speech and improve coding performance when divided parameter code embedding is carried out.

Although with this embodiment a case has been described where CELP coding is used in speech coding, using CELP coding is by no means required for the present invention, and it is possible to achieve the same operation effects as described above using other speech coding schemes.

Further, some or all of the inactive speech parameters may also be shared with normal speech coding parameters. For example, when LPC parameters of the inactive speech parameters are used in spectrum shape information, this LPC parameter quantization code is made the same as quantization code for the LPC parameters used at LPC quantizer 208 or the same as part of it. By this means, it is possible to improve quantization performance when embedding (for example, replacement and overwriting) of inactive speech parameter coded data is carried out.

Further, with this embodiment, a case has been described where LPC quantization code and quantized fixed excitation gain code is assumed to be coded data subjected to embedding of inactive speech parameter coded data. However, coded data subjected to embedding is by no means limited to this, and other coded data may also be adopted and subjected to embedding.

Embodiment 3

Figure 11A:
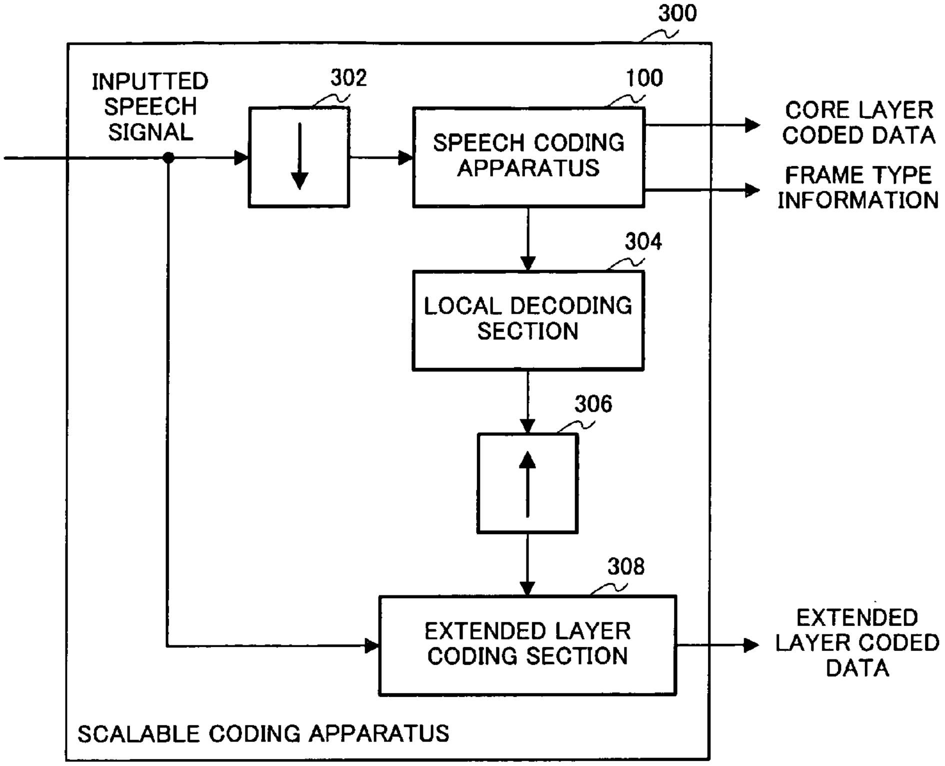
FIG. 11A is a block diagram showing a configuration of a scalable coding apparatus of Embodiment 3 of the present invention.
Figure 11B:
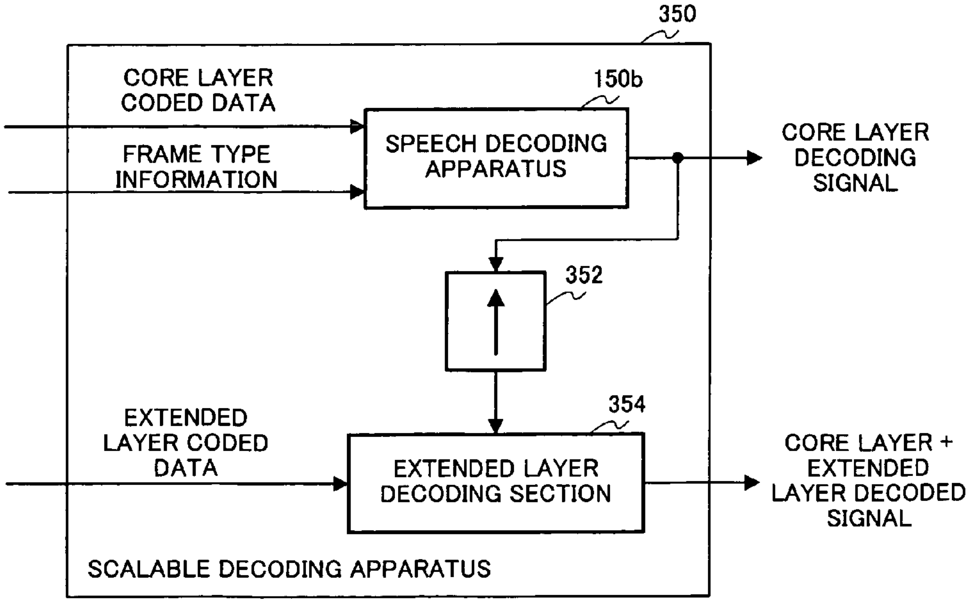
FIG. 11B is a block diagram showing a configuration of a scalable decoding apparatus of Embodiment 3 of the present invention.

FIG. 11A and FIG. 11B are block diagrams showing a scalable coding apparatus and scalable decoding apparatus of Embodiment 3 of the present invention. With this embodiment, a case will be described where the apparatuses described in Embodiment 1 (or Embodiment 2) are applied to a speech coded core layer having a bandwidth scalable function as a scalable configuration.

Scalable coding apparatus 300 shown in FIG. 11A has: down-sampling section 302; speech coding apparatus 100; local decoding section 304; up-sampling section 306; and extended layer coding section 308.

Down-sampling section 302 carries out down-sampling an inputted speech signal to a signal of a core layer bandwidth. Speech coding apparatus 100 has the same configuration as described in Embodiment 1, generates coded data and frame type information from the inputted speech signal, and outputs these. The generated coded data is then outputted as core layer coded data.

Local decoding section 304 carries out local decoding on core layer coded data, and obtains a core layer decoded speech signal. Up-sampling section 306 carries out up-sampling of a core layer decoded speech signal to a signal of a bandwidth of an extended layer. Extended layer coding section 308 carries out extended layer coding on the inputted speech signal having an extended layer signal bandwidth, and generates and outputs extended layer coded data.

Scalable decoding apparatus 350 shown in FIG. 11B has speech decoding apparatus 150*b*, up-sampling section 352 and extended layer decoding section 354.

Speech decoding apparatus 150*b* has the same configuration as described in Embodiment 1, generates a decoded speech signal from core layer coded data and frame type information transmitted from scalable coding apparatus 300, and outputs this as a core layer decoded signal.

Up-sampling section 352 carries out up-sampling of a core layer decoded signal to a signal of a bandwidth of an extended layer. Extended layer decoding section 354 decodes extended layer coded data transmitted from scalable coding apparatus 300 and obtains an extended layer decoded signal. Extended layer decoding section 354 then generates a core layer+extended layer decoded signal by multiplexing core layer decoded signals subjected to up-sampling to an extended layer decoded signal, and outputs this.

Scalable coding apparatus 300 may also have speech coding apparatus 200 described in Embodiment 2 in place of speech coding apparatus 100 described above.

The operations of scalable decoding apparatus 350 having the above configuration will be described. Assume that, at a core layer, frame format switching control is not carried out. In this case, it is possible to obtain the core layer+extended layer decoded signal. Further, assume that setting is carried out so that only the core layer is decoded, and frame format switching control is carried out at the core layer. In this case, it is possible to obtain a decoding signal having the highest coding efficiency and a low bit rate. Further, assume that, at inactive speech frames, setting is carried out so as to decode only the core layer with frame format switching control, and, at active speech frames, setting is carried out so as to decode frame layer+extended layer. In this case, it is possible to achieve intermediate speech quality and transmission efficiency between the two cases described above.

In this way, according to this embodiment, it is possible to select and decode a plurality of types of decoding speech signals on a decoding side (or on a network) without dependent on the setting conditions for control on the coding side.

In addition, each function block employed in the description of the above-mentioned embodiments may typically be implemented as an LSI constituted by an integrated circuit. These may be individual chips or partially or totally contained on a single chip.

"LSI" is adopted here but this may also be referred to as "IC," "system LSI," "super LSI", or "ultra LSI" depending on differing extents of integration.

Further, the method of integrating circuits is not limited to LSI's, and implementation using dedicated circuitry or general purpose processors is also possible. After LSI manufacture, utilization of an FPGA (Field Programmable Gate Array) or a reconfigurable processor where connections and settings of circuit cells within an LSI can be reconfigured is also possible.

Further, if integrated circuit technology comes out to replace LSI's as a result of the advancement of semiconductor technology or a derivative other technology, it is naturally also possible to carry out function block integration using this technology. Application in biotechnology is also possible.

This application is based on Japanese Patent Application No. 2004-216127, filed on Jul. 23, 2004, the entire content of which is expressly incorporated by reference herein.

INDUSTRIAL APPLICABILITY

The speech coding apparatus and speech coding method of the present invention are useful for transmitting coded data of different format types between active speech sections and inactive speech sections.

The invention claimed is:

1. A speech coding apparatus that encodes a speech signal which has an active speech component and an inactive speech component, the speech coding apparatus comprising:

a first coder that encodes by a first coding method a segment of the speech signal to generate first coded data;

a second coder that encodes by a second coding method that is different from the first coding method the segment of the speech signal to generate second coded data, which differs from the first coded data, when the segment of the speech signal is inactive speech;

a first determination section that determines whether the segment of the speech signal is active speech or inactive speech;

a second determination section that determines whether to use the second coded data when the segment of the speech signal is inactive speech; and an embedding section that overwrites a portion of the first coded data with the second coded data, wherein the portion of the first coded data being overwritten has less than a predetermined sensitivity, when the first determination section determines that the segment of the speech signal is inactive speech and the second determination section determines that the second coded data is to be used.

2. The speech coding apparatus of claim 1, wherein the first and second coded data for the inactive speech segment represent noise within the speech signal.

3. The speech coding apparatus of claim 1, wherein a predetermined position of the first coded data is overwritten with the second coded data.

4. The speech coding apparatus of claim 1, wherein:

the first coder creates a data frame, which contains only the first coded data upon its creation, and the embedding section replaces one or more bits of the first coded data with one or more bits of the second coded data.

5. The speech coding apparatus of claim 1, wherein:

the first coder creates a data frame, which contains only the first coded data upon its creation, and the embedding section overwrites one or more bits of the first coded data with one or more bits of the second coded data.

6. The speech coding apparatus of claim 1, wherein:

the first coder creates a data frame, which contains only the first coded data upon its creation, the embedding section replaces a number of bits of the first coded data with bits of the second coded data, and the number of bits represent speech signal information having less than a predetermined sensitivity.

7. The speech coding apparatus of claim 1, wherein:

the first coder creates a data frame, which contains only the first coded data upon its creation, the embedding section replaces a number of bits of the first coded data with bits of the second coded data, and the number of bits represent speech signal information having the lowest sensitivity.

8. The speech coding apparatus of claim 1, wherein the first coder selects one of a plurality of coding schemes for encoding the segment of the speech signal.

9. A speech decoding apparatus that decodes encoded data of a speech signal which has an active speech component and an inactive speech component, the speech decoding apparatus comprising:

a first decoder that decodes by a first decoding method first encoded data of the speech signal to generate first decoded data;

a second decoder that decodes by a second decoding method that is different from the first decoding method second encoded data, which differs from the first encoded data, of the speech signal to generate second decoded data; and a selection section that selects one of the first and second decoded data to represent the speech signal, wherein the second encoded data, with which the first encoded data has been overwritten by an encoder, is extracted from the first encoded data, wherein a portion of the first encoded data being overwritten has less than a predetermined sensitivity.

10. A speech coding method for encoding a speech signal which has an active speech component and an inactive speech component, the method comprising:

encoding by a first encoding method a segment of the speech signal to generate first coded data;

encoding by a second coding method that is different from the first coding method the segment of the speech signal to generate second coded data, which differs from the first coded data, when the segment of the speech signal is inactive speech;

determining whether the segment of the speech signal is active speech or inactive speech;

determining whether to use the second coded data when the segment of the speech signal is inactive speech; and overwriting, with an integrated circuit or computer processor, a portion of the first coded data with the second coded data when the segment of the speech signal is determined to be inactive speech and the second coded data is determined to be used, wherein the portion of the first coded data being overwritten has less than a predetermined sensitivity.

11. A speech decoding method for decoding encoded data of a speech signal which has an active speech component and an inactive speech component, the method comprising:

decoding by a first decoding method first encoded data of the speech signal to generate first decoded data;

decoding by a second decoding method that is different from the first decoding method second encoded data, which differs from the first encoded data, of the speech signal to generate second decoded data; and selecting, with an integrated circuit or computer processor, one of the first and second decoded data to represent the speech signal, wherein the second encoded data, with which the first encoded data has been overwritten by an encoder, and is extracted from the first encoded data, wherein a portion of the first encoded data being overwritten has less than a predetermined sensitivity.

12. A scalable coding apparatus comprising:

a down-sampling section that carries out down-sampling on a speech signal inputted from outside, to a signal of a core layer bandwidth;

the speech coding apparatus of claim 1 that receives the speech signal subjected to down-sampling by the down-sampling section as input, generates the first and second coded data, and synthesizes part of the first coded data using the second coded data to produce core layer coded data;

a decoding section that carries out local decoding an the core layer coded data outputted from the speech coding apparatus to obtain a core layer decoded speech signal;

an up-sampling section that carries out up-sampling on the decoded speech signal obtained by the decoding section, to a signal of an extended layer bandwidth; and an extended layer coding section that carries out extended layer coding, based on the decoded speech signal subjected to up-sampling by the up-sampling section and the speech signal inputted from outside, and generates and outputs extended layer coded data.

13. A scalable decoding apparatus comprising:

the speech decoding apparatus of claim 9 that receives first coded data and second coded data as input, as core layer coded data, and outputs the first decoded data or the second decoded data, as core layer decoded data;

an up-sampling section that carries out up-sampling on the core layer decoded data outputted from the speech decoding apparatus, to a signal of an extended layer bandwidth; and an extended layer decoding section that decodes extended layer coded data inputted from outside to obtain an extended layer decoded signal, and multiplexes the core layer decoded data subjected to up-sampling by the up-sampling section on the extended layer decoded signal.

14. A scalable coding method comprising:

carrying out down-sampling on a speech signal inputted from outside to a signal of a core layer bandwidth;

encoding the speech signal subjected to down-sampling by the speech coding method of claim 10, generating the first and second coded data, and synthesizing part of the first coded data using the second coded data to produce core layer coded data;

carrying out local coding on the core layer coded data to obtain a core layer decoded speech signal;

carrying out up-sampling on the decoded speech signal to a signal of an extended layer bandwidth; and carrying out encoding on the extended layer based on the decoded speech signal subjected to the up-sampling and the speech signal inputted from outside, and generating and outputting extended layer coded data.

15. A scalable decoding method comprising:

receiving first encoded data and second encoded data as input, as core layer coded data, and decoding the first and second encoded data of the core layer coded data by the speech decoding method of claim 11 so as to generate and output the first decoded data or the second decoded data, as core layer decoded data;

carrying out up-sampling on the core layer decoded data to a signal of an extended layer bandwidth; and decoding extended layer coded data inputted from outside to obtain an extended layer decoded signal, and multiplexing the core layer decoded data subjected to the up-sampling on the extended layer decoded signal.

* * * * *